United States Patent [19]

Langley et al.

[11] Patent Number: 4,969,472

[45] Date of Patent: Nov. 13, 1990

[54] PERIMETER GARTER FOR EYE PATCHES

[75] Inventors: Eleanor Langley, Corona Del Mar; Marc Weintraub, Laguna Niguels, both of Calif.

[73] Assignee: Dioptics Medical Products, Inc., San Luis Obispo, Calif.

[21] Appl. No.: 420,179

[22] Filed: Oct. 12, 1989

[51] Int. Cl.[5] .............................................. A61F 9/00
[52] U.S. Cl. ........................................ 128/858; 2/15
[58] Field of Search ................. 128/161, 164, 203.29, 128/206.28, 853, 858; 2/2, 15, 439, 440; 206/805

[56] References Cited

U.S. PATENT DOCUMENTS

| | | | |
|---|---|---|---|
| 3,052,887 | 9/1962 | Sockel et al. | 2/2 X |
| 3,331,105 | 7/1967 | Gordon | 206/805 X |
| 3,572,396 | 3/1971 | Hoffman et al. | 206/805 X |
| 4,043,329 | 8/1977 | DiMatteo | 128/161 X |
| 4,707,863 | 11/1987 | McNeal | 2/439 X |

*Primary Examiner*—Robert A. Hafer
*Assistant Examiner*—Kerry Owens
*Attorney, Agent, or Firm*—Knobbe, Martens, Olson & Bear

[57] ABSTRACT

The present invention provides an inexpensively formed perimeter garter for use with eye patches during a post-surgery or post-injury period. The perimeter garter comprises a strip taken from a flat sheet of resilient foam material and formed into a closed curve. The perimeter length of the garter is less than the perimeter length of the eye patch by an amount which causes the garter to stretch around the perimeter of the eye patch and fold down on the opposite sides of the eye patch to lie relatively flat against the sides.

4 Claims, 1 Drawing Sheet

U.S. Patent          Nov. 13, 1990          4,969,472
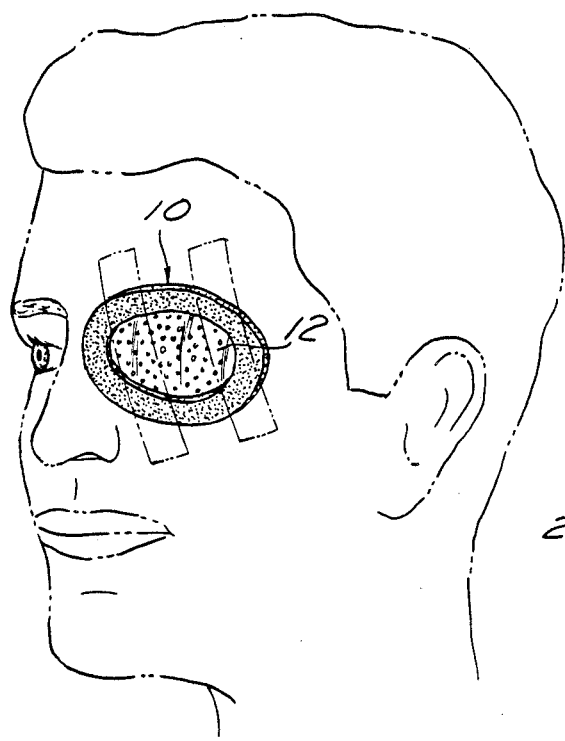
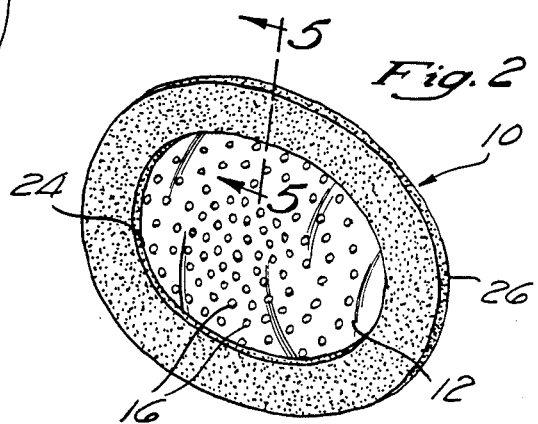
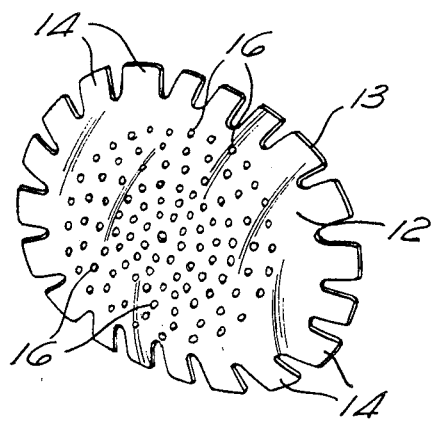
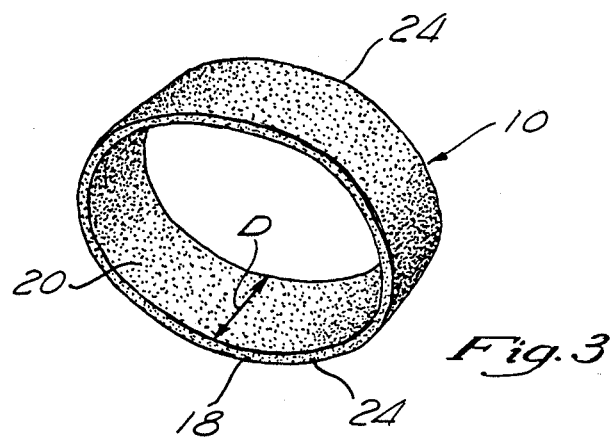
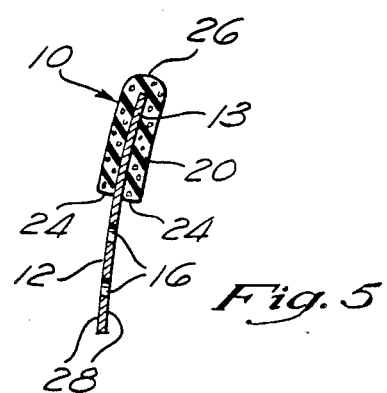

PERIMETER GARTER FOR EYE PATCHES

FIELD OF THE INVENTION

The present invention relates generally to the field of eye care devices for post-surgery or post-injury utility, or the like. More specifically, the invention relates to perimeter garters used with protective eye patches or eye shields, and most specifically to inexpensively formed perimeter garters and a method for forming such perimeter garters.

BACKGROUND OF THE INVENTION

It is common practice to wear eye patches during a post-surgery period or after injury to the eyes. During this time it is especially critical to protect the eyes since they are particularly sensitive to bright lights and susceptible to infection. Presently, there are a variety of protective eye patches available on the market. Eye patches are typically formed from a suitable rigid material such as plastic, some kind of metal (preferably aluminum), or the like. Eye patches are commonly configured in suitable shapes to cover the eye and its surrounding area. Some eye patches have a uniform circumference and others, particularly those made from aluminum, have a serrated edge.

A common drawback with existing eye patches is that the rigid circumference, whether uniform or serrated, penetrates or applies pressure against the area surrounding the eye, which might already be inflamed and sensitive. This causes discomfort and sometimes additional injury. Therefore, to prevent additional injury or trauma, protective devices made of soft material are commonly stretched over the perimeter of the patch and used to protect the skin from the rigid edge. An existing concern with such devices which are utilized for this purpose is that they are often more expensive than the patch itself, and thus significantly increase the cost of the combination to the patient. Furthermore, these devices tend to slip off the edge of the patch. Once the perimeter garter is displaced, the rigid edge of the eye patch is again exposed.

The most common commercially available devices are manufactured of cloth woven from elastic material. Such devices comprise a circular strip of such cloth, wherein the edges of the strip are bound with elastic binding thread, so that the edges have a smaller relaxed diameter than the central portion of the strip. This configuration causes the strip, even in its relaxed state, to form a configuration resembling an automobile tire, i.e., a circular strip with its edges folded inwardly toward the center. When these strips are stretched around an eye patch, the added resiliency at the edges of the strips assures that the garter will closely conform to the edge of the patch, and will lie flat against both the front and back surfaces of the patch.

Such a construction helps to prevent the strip from slipping away from the edge of the patch. However, this woven and bound construction requires a considerable amount of hand labor which substantially increases manufacturing costs.

SUMMARY OF THE INVENTION

The present invention provides an improved and inexpensively formed perimeter garter which can be used with any available eye patch. The patch provided by this invention tightly conforms to the edge of the patch, as well as the front and rear faces adjacent the edge, reducing the likelihood that the garter will slip out of place. Furthermore, the garter may be formed from material which has a soft or supple surface configuration, making it comfortable for the wearer. This supple surface also tends to cling to the surface of the patch, eliminating further any likelihood that the garter will slip from the edge of the patch.

The present invention additionally provides a method for making such perimeter garters from inexpensive materials, without substantial hand labor, thus significantly reducing their cost.

In accordance with a preferred embodiment of the present invention, the perimeter garter is formed by first rolling a sheet of thin foam material into a cylinder, and bonding the rolled edges together to form an open tube. This tube is then sliced, as one would slice a loaf of bread, to form a large number of short cylinders. Each of these short cylinders provides a garter for surrounding and protecting the edge of one eye patch. As thus formed, each garter comprises a single circular strip of resilient material, preferably foamed plastic material. The strip is formed into a cylinder by joining the ends of the strip together. The garter advantageously has a perimeter length less than that of the eye patch. Thus, when the garter is placed around the eye patch, the resiliency of the material permits the garter to be stretched around the circumference of the eye patch. The difference between the perimeter length of the garter and the patch is sufficient so as to cause the stretched garter to fold along its opposite edges to lie relatively flat against the front and back sides of the eye patch. In one aspect of the invention, the perimeter length of the garter is less than the perimeter length of the eye patch by an amount which is calculated using a formula which assures that the garter edges will lie flat against the eye patch.

BRIEF DESCRIPTION OF THE DRAWINGS

The preferred embodiment of the invention is illustrated in and by the following drawings in which like reference numerals indicate like parts and in which:

FIG. 1 is a front perspective view illustrating a protective eye patch covering a patient's eye. The eye patch is surrounded by a perimeter garter of the preferred embodiment of the present invention.

FIG. 2 is a front perspective view illustrating the manner in which the perimeter garter of the present invention stretches around the circumference of the eye patch and folds down on its opposite sides to lie relatively flat against the opposite sides of the eye patch.

FIG. 3 is a perspective view illustrating the perimeter garter of the present invention formed in a closed curve.

FIG. 4 is a perspective view of a prior art eye patch.

FIG. 5 is a cross sectional view taken along line 5—5 of FIG. 2, additionally illustrating that the perimeter length of the garter is less than the perimeter of the eye patch by an amount which causes the edges of the garter to conform closely to the faces of the eye patch.

DETAILED DESCRIPTION OF A PREFERRED EMBODIMENT

Referring now to the drawings, FIG. 1 illustrates generally a perimeter garter 10 in accordance with the preferred embodiment of the present invention. Such a perimeter garter 10 may be utilized with any type of presently available eye patch 12. In general, the eye patch 12 is constructed from a suitably rigid material such as plastic or metal, such as aluminum. As shown, the eye patch/garter combination may be taped onto the face of the patient. Alternatively, an elastic headband may be used to encircle the patient's head and hold the patch 12 in place. Because the edges of the patch 12 only generally conform to the contours of the user's face, the garter 12 should be thick enough and resilient enough to seal against the surface of the patient's skin and fill voids between the patch 12 and those contours. While some metal patches 12, such as those made from relatively soft aluminum, may be bent to conform more closely to the face, even these patches cannot conform perfectly without a resilient member at their edges.

Furthermore, it will be recognized that the patches 12 are relatively thin, and thus have thin edges which may cause discomfort to the patient. The resilience and softness of the patch 10 are thus important in providing comfort to the patient, especially during periods of extended use.

Referring now to FIG. 4, there is illustrated a typical prior art eye patch 12 made from aluminum. The eye patch 12 is somewhat elliptical in shape. Along an outer edge or perimeter 13, the eye patch 12 is serrated, providing a plurality of protrusions 14. These protrusions may be individually bent out of the principal plane of the patch 12 to create an undulating edge which conforms to the contour of the user's face. While this is advantageous, it makes the use of a protective garter a practical necessity, since the naked protrusions 14 would otherwise add to patient discomfort. Other eye patches may alternatively have uniform outer edges. The eye patch 12 additionally comprises a plurality of equally spaced pores 16 to provide a steady inflow of air. While such pores would admit light, cotton, gauze or other material, is typically placed behind the patch if it is desired to exclude all light.

Referring now to FIG. 3, the perimeter garter 10 is formed into a closed curve 18. The perimeter garter 10 of the preferred embodiment is advantageously formed by rolling a sheet of foamed plastic into a cylinder, and, after joining the ends of the rolled sheet permanently together, slicing the cylinder to form plural circular strips. One such circular strip, or short cylinder of foam, is shown at 20, and forms the garter 10. The edges of the sheet may be joined using any of the common techniques in the art for joining foam plastic, such as gluing or heat bonding. In this exemplary embodiment, the ends of the strip 20 are heat bonded to form a permanent seam.

The perimeter garter 10 thus forms a short cylinder, having a pair of circular edges 24. The two circular edges 24 are separated by the cylinder length, which is labeled D in FIG. 3.

Referring now to FIGS. 2 and 5, the perimeter garter 10 is shown stretched over the edge of the patch 12, covering the serrations 14 (FIG. 4), and entirely surrounding the patch. The garter 10 is not affixed to the patch, but is instead held in place by its own resilience. To accomplish this, the garter has a perimeter length in its relaxed state (18 in FIG. 3) which is considerably shorter than the perimeter length of the patch (13 in FIG. 4). This length difference is important, since it must be sufficient to permit the strip 20, due to its resiliency, to stretch around the perimeter of the eye patch 12 while at the same time assuring that the edges 24 fold around the edge 13 off the patch and lie flat against the front and back faces 28 of the patch 12, as shown in FIG. 5. The strip 20 thus resiliently displaces from its relaxed cylindrical configuration to a conforming shape similar to that of a tire. The strip 20 has a maximum tension around its center 26 and a relatively reduced tension around its perimeter edges 24.

From FIG. 5 it can be seen that, in order to assure that the edges of the garter 10 lie flat against the surfaces of the patch, the perimeter length of the edges 24 of the garter 10, in its installed position, must exceed the perimeter length of the edges 24 in the relaxed position (FIG. 3). That is, the edges 24 must be under some tension in the installed position, or they would flare away from the surfaces of the patch. From this relationship, it is possible to determine the required relaxed diameter of the garter 10.

If it is assumed that the perimeter of the eye patch can be approximated as a circle, and the diameter of the patch 12 is $P_1$, then the perimeter of the eye patch, and also of the central portion of the garter 10 which fits around the outer edge of the patch 12 must be approximately $R_1 = \pi(P_1)$ in its in-use configuration. Although there is tension on the garter 10, the width D, shown in FIG. 3, does not change appreciably when the garter 10 is installed on the patch 12. Thus, the diameter of the edge 24 in the installed or in-use configuration is: $P_2 = P_1 - D$. The perimeter length of the edge 24 in the installed or in-use configuration is thus: $R_2 = \pi(P_2) = \pi(P_1 - D)$. Because, as explained above, the perimeter length $R_2$ in the in-use configuration must be larger than the perimeter length of the strip in its relaxed configuration (FIG. 3), the preferable maximum perimeter length of the relaxed garter (FIG. 3) is $\pi$ times the difference between the perimeter length of the eye patch 12 and the width D of the garter.

Although this invention has been described in terms of the preferred embodiment, other embodiments that are apparent to those of ordinary skill in the art are also within the scope of the invention. Accordingly, the scope of the invention is intended to be defined only by reference to the appended claims.

We claim:

1. An eye care kit for post-surgery or post-injury utility, comprising:
    a protective eye patch having two opposite faces and a first perimeter length; and
    a perimeter garter for use with said eye patch, said garter comprising:
        at least one strip having two perimeter edges, said strip taken from a flat sheet of foamed plastic material and formed into a closed curve, said closed curve having a second perimeter length, said second perimeter length being less than said first perimeter length by a predetermined amount, said predetermined amount causing said strip to stretch around said first perimeter length of said eye patch and fold said perimeter edges of said strip around the edge of said eye patch and lie flat against said opposite faces of said eye patch.

2. An eye care kit as defined in claim 1, wherein said strip has a fixed width and said second perimeter length of said perimeter garter is less than said first perimeter length of said eye patch by an amount which is greater than said width multiplied by Pi ($\pi$).

3. A method of forming and applying perimeter garters for protective eye patches, said eye patch having a first perimeter length, comprising the steps of:
    providing a flat sheet of foamed plastic material;

forming at least one strip from said flat sheet into a closed curve having a second perimeter length which is less than said first perimeter length; and stretching said strip around the perimeter of said protective eye patch, the difference between said first and second perimeters being sufficient so that said stretching folds the opposite sides of said strip around the edge of said protective eye patch to lie relatively flat against opposite sides of said protective eye patch.

4. An improved method of inexpensively forming and applying a perimeter garter for a protective eye patch, comprising the steps of:

joining at least one flat strip of foam material to form a closed curve;

stretching said closed curve around the perimeter of said protective eye patch to fold down the opposite sides of said strip to lie relatively flat against the faces of said protective eye patch.

* * * * *